United States Patent
Collins et al.

(10) Patent No.: US 6,227,041 B1
(45) Date of Patent: *May 8, 2001

(54) METHOD AND APPARATUS FOR MEASURING VOLATILE CONTENT

(75) Inventors: Michael J. Collins, Charlotte; William Edward Jennings, Wingate, both of NC (US)

(73) Assignee: CEM Corporation, Matthews, NC (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/156,086

(22) Filed: Sep. 17, 1998

(51) Int. Cl.[7] ............................ G01N 5/02; G01N 25/56; G01G 23/48

(52) U.S. Cl. ..................... 73/76; 374/14; 219/711

(58) Field of Search ................. 73/76; 177/245; 374/14; 119/710, 711, 712

(56) References Cited

U.S. PATENT DOCUMENTS

| | | | |
|---|---|---|---|
| 3,292,417 | * 12/1966 | Hayden et al. | 374/14 |
| 3,534,260 | 10/1970 | Walker . | |
| 3,693,079 | 9/1972 | Walker . | |
| 3,813,918 | 6/1974 | Moe . | |
| 3,902,354 | * 9/1975 | Harlan et al. | 374/14 |
| 3,909,598 | * 9/1975 | Collins et al. | 702/30 |
| 4,291,775 | * 9/1981 | Collins | 73/76 |
| 4,304,289 | 12/1981 | McMullen . | |
| 4,447,693 | 5/1984 | Buck . | |
| 4,484,133 | 11/1984 | Riggin . | |
| 4,485,284 | 11/1984 | Pakulis | 374/14 |
| 4,554,132 | * 11/1985 | Collins | 73/76 X |
| 4,566,804 | * 1/1986 | Collins et al. | 374/14 |
| 4,578,998 | 4/1986 | Gard . | |
| 4,600,879 | 7/1986 | Scully et al. . | |
| 4,606,650 | 8/1986 | Harris | 374/14 |
| 4,674,325 | 6/1987 | Kiyobe et al. . | |
| 4,709,579 | 12/1987 | Parker et al. . | |
| 4,716,360 | 12/1987 | Pakulis . | |
| 4,750,143 | 6/1988 | Heintz et al. | 73/76 |
| 4,767,982 | 8/1988 | Florig et al. . | |

(List continued on next page.)

FOREIGN PATENT DOCUMENTS

| | | | |
|---|---|---|---|
| 0344465 | 12/1989 | (EP) | 73/76 |
| 2202054 | 9/1988 | (GB) | 73/76 |

*Primary Examiner*—Daniel S. Larkin
(74) *Attorney, Agent, or Firm*—Philip Summa, P.A.

(57) ABSTRACT

A method and associated apparatus are disclosed for measuring volatile content of samples that are particularly suitable for samples that tend to burn when heated. The method includes the steps of applying microwave radiation at a predetermined power level to a moisture-containing sample to drive volatiles from the sample, monitoring the weight of the sample during the application of microwave power, monitoring the temperature of the sample during the application of microwave power without contacting either the sample or anything in contact with the sample, and moderating the microwave power being applied to the sample based upon the monitored temperature to maintain the temperature of the sample at or below a pre-determined set point temperature below which the sample will not burn. In its apparatus aspects, the invention includes a cavity for holding a sample for which the volatile content is to be determined; an infrared photosensor positioned to measure the temperature of a sample placed within the cavity, an analytical balance for measuring the weight of the sample while the sample is in the cavity, a power source for introducing microwaves into the cavity, and a processing unit in communication with the infrared photosensor and the power source for controlling the introduction of microwave energy to the cavity in response to the infrared photosensor to prevent the sample from reaching temperatures at which the sample would burn.

38 Claims, 2 Drawing Sheets

U.S. PATENT DOCUMENTS

| | | |
|---|---|---|
| 4,771,631 | 9/1988 | Lehtikoski et al. . |
| 4,787,052 | 11/1988 | Yamaguchi . |
| 4,798,252 * | 1/1989 | Knothe et al. ........................ 73/76 X |
| 4,835,354 * | 5/1989 | Collins et al. ........................ 219/711 |
| 4,970,374 | 11/1990 | Ueda et al. . |
| 4,977,377 | 12/1990 | Durrett et al. . |
| 5,001,434 | 3/1991 | Marrelli et al. . |
| 5,014,010 | 5/1991 | Helms et al. . |
| 5,046,356 | 9/1991 | Osaki et al. ........................... 73/73 |
| 5,086,279 | 2/1992 | Wochnowski et al. . |
| 5,237,142 | 8/1993 | Cigarini et al. ...................... 219/710 |
| 5,256,978 | 10/1993 | Rose . |
| 5,589,094 * | 12/1996 | Bu ..................................... 219/710 X |
| 5,796,080 | 8/1998 | Jennings et al. . |
| 5,919,389 * | 7/1999 | Uehashi et al. ...................... 219/711 |
| 5,983,711 * | 11/1999 | Pappas et al. .......................... 73/76 |

\* cited by examiner

METHOD AND APPARATUS FOR MEASURING VOLATILE CONTENT

FIELD OF THE INVENTION

The invention relates to methods and apparatuses for measuring volatile content of a sample using microwave radiation. More particularly, the invention pertains to a method and an apparatus that helps to control sample temperatures during volatile content analyses.

BACKGROUND OF THE INVENTION

Measuring the sample volatile content (which in many cases is the moisture content) is a frequent and repetitive chore in many analytical laboratories. In its simplest form, determining volatile or moisture content consists of weighing a representative sample of material, drying the material, then re-weighing the material to ascertain the losses on drying and, consequently, the initial volatile content of the sample. Convective, hot-air ovens, which are typically used for this task, can be relatively slow to bring the sample to "oven-dry" equilibrium. Such devices can also be expensive to operate as they inefficiently consume energy. These problems lessen the utility of hot-air devices for volatile analysis.

Drying substances using microwave energy to determine volatile or moisture content is generally convenient and precise. More importantly, microwave drying to measure moisture content is usually faster than equivalent hot-air methods. As in hot-air techniques, however, certain substances tend to burn, rather than merely become dry, when microwave power is applied to them. Stated differently, the rapid manner in which microwaves tend to interact with certain materials-which is an obvious advantage in some circumstances-can cause secondary heating of other materials that is disadvantageous (at least for volatile or moisture measurement purposes). Certain food products such as cheese are exemplary (although certainly not limiting) of materials that tend to burn rather than dry.

Additionally, microwaves interact with materials in a fashion known as "coupling," i.e., the response of the materials ("the load") to the microwave radiation. Some materials do not couple well with microwave energy, making drying or other volatile removal techniques difficult or imprecise. Other materials couple well when their moisture content or content of other microwave-responsive materials (e.g., alcohols and other polar solvents) is high. As they dry under the influence of microwaves, however, they couple less and less effectively; i.e., the load changes. As a result, the effect of the microwaves on the sample becomes less satisfactory and more difficult to control. In turn, the sample can tend to burn rather than dry, or degrade in some other undesired fashion. Both circumstances, of course, tend to produce unsatisfactory results.

As another factor, volatiles such as "loose" water (i.e., not bound to any compound or crystal) respond quickly to microwave radiation, but "bound" water (e.g., sodium carbonate monohydrate, $Na_2CO_3.H_2O$) is typically unresponsive to microwave radiation. Instead, such bound water must be driven off thermally; i.e., by heat conducted from the surroundings. The nature of microwave radiation is such, however, that not all such surroundings may be heated when exposed to microwaves. Thus, the simple application of microwaves is typically less satisfactory for determining bound water than are more conventional heating methods.

Maintaining the sample's temperature below that which will cause pyrolysis helps prevent burning. To the extent moisture analysis is based upon weight measurements, however, measuring the sample's temperature cannot be permitted to hinder measuring the sample's weight. Thus, conventional direct probe temperature measurement is often unsatisfactory for this purpose. The temperature sensor's contact with the sample can lead to erroneous weight measurements when using sensitive weighing devices. Furthermore, in a microwave environment, the type, location, and function of a temperature probe must be compatible with the proper propagation of energy to, and absorption of energy by, the sample.

Some indirect methods have been developed to measure temperature in a way that avoids contacting the sample in an effort to avoid interfering with measuring sample weight. Many such indirect techniques, however, determine the temperature of something besides the sample itself. Thus, such techniques can lack accuracy, and can give a relatively slow response, particularly when heat conduction from the sample to the sensor is required.

Therefore, a need exists for taking advantage of the rapid response characteristics of microwave heating, while avoiding burning the sample, and while measuring the sample weight on a continuous basis that provides quick results.

OBJECT AND SUMMARY OF THE INVENTION

It is an object of the invention to quickly measure the volatile content of a sample in a way that will neither burn the sample nor interfere with the measurement of sample weight. Accordingly, the invention is an apparatus and method for quickly determining sample volatile content, and usually moisture content, through losses on drying while controlling the sample's temperature. In particular, this invention provides quick and accurate moisture analysis while helping to prevent sample burning.

The method includes initially measuring sample weight and sample temperature. Then, microwave radiation is introduced to the sample to drive off moisture or other volatiles. Meanwhile, the changes to the sample weight and sample temperature are monitored. The introduction of microwave radiation is varied to maintain sample temperature at a set point or within a set range chosen to prevent sample pyrolysis. Once the incremental change to the weight of the sample reaches or approaches equilibrium, the introduction of microwave radiation is stopped. Thereafter, the moisture content of the sample is calculated.

The apparatus includes a structure forming an enclosed cavity to hold a sample and to contain microwave radiation, a microwave power source, a means to measure sample weight, a means to measure sample temperature, and a controller that moderates the introduction of microwave radiation to the sample based upon the sample temperature. The controller is programmed to moderate the applied microwave power (the manipulated variable) to maintain the sample's temperature at a set point or within a set range.

The foregoing and other objects and advantages of the invention and the manner in which the same are accomplished will become clearer based on the following detailed description taken in conjunction with the accompanying drawings in which:

DETAILED DESCRIPTION OF THE INVENTION

The invention is an apparatus and associated method for measuring the moisture (or other volatile) content of a sample that is particularly suitable for samples that tend to burn when heated. The apparatus is broadly designated at 10 in FIG. 1 and in schematic fashion at 20 in FIGS. 2 and 3.

The apparatus 10 includes a cavity 11 defined by the interior walls of the apparatus 10 or 20 for holding a sample 12 for which the moisture content is to be determined. As used herein, the term "cavity" is used in its broadest sense to refer to any defined location to which the microwaves are directed. For various health and safety reasons, microwave analytical techniques are generally carried out within appropriate barriers that prevent the microwaves from propagating into the ambient surroundings. Metal walls or screens are most typically used for these purposes. It will be understood, however, that other cavity designs, shapes, and equipment can be used consistently with the present invention.

Figure 1:
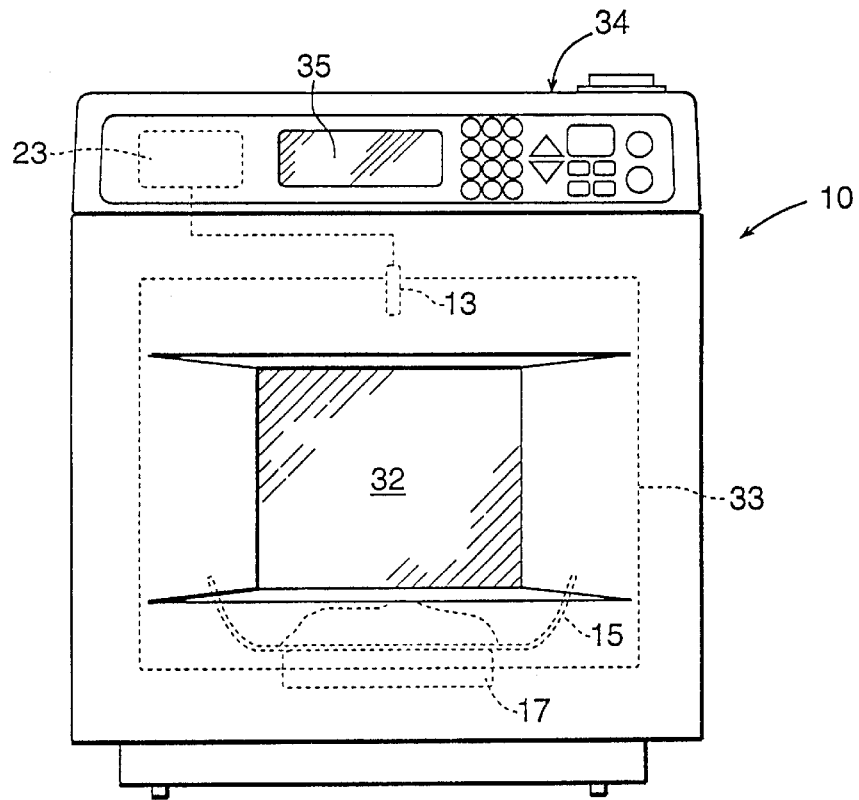
FIG. 1 is a frontal perspective view of the moisture-content apparatus of the present invention showing the microwave chamber, the processing unit, and a viewing window.
Figure 2:
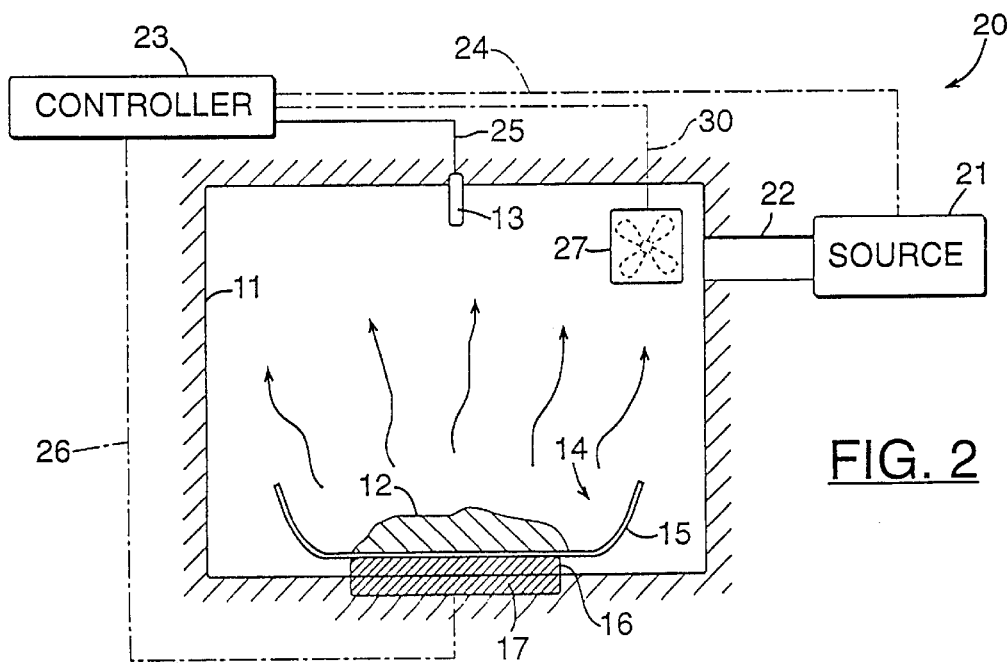
FIG. 2 is schematic view of the invention showing an analytical balance, the microwave generator, the variable-speed fan, and the controller.
Figure 3:
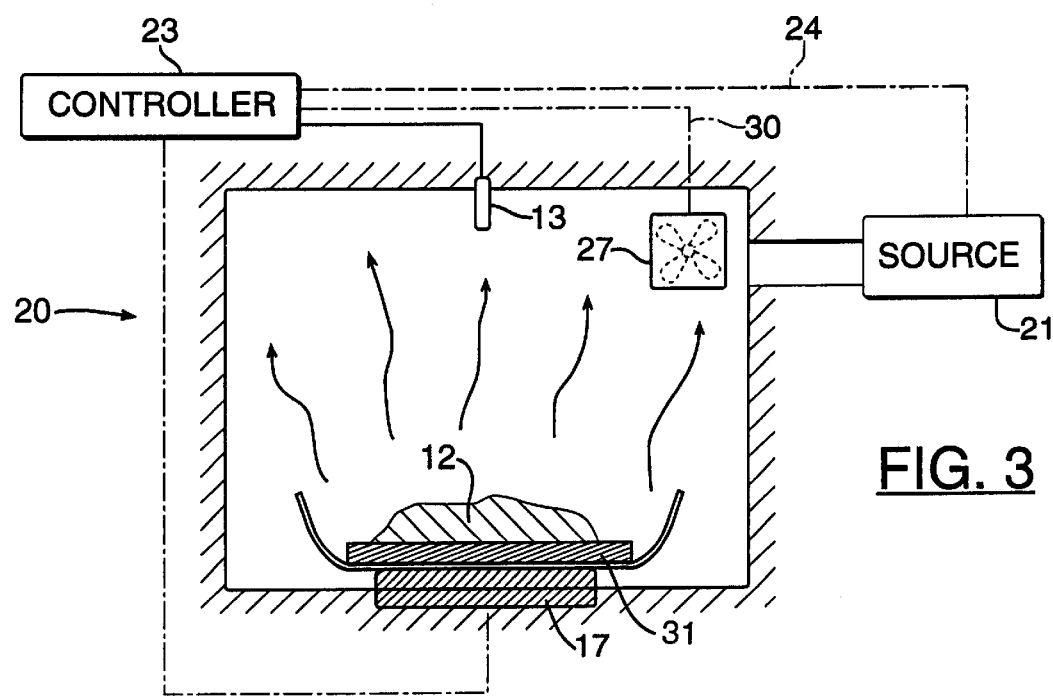
FIG. 3 is a schematic view showing another embodiment of the invention that includes the analytical balance, the microwave generator, the variable-speed fan, the controller, and a susceptor.

The apparatus includes an infrared photosensor 13 positioned to measure the temperature of the sample 12 placed within the cavity 11. As illustrated in FIGS. 1–3, the infrared photosensor 13 is positioned within the cavity 11, but it will be understood, particularly in conjunction with the method aspects of the invention, that the location of the photosensor 13 is limited only by the requirement that it be able to detect infrared radiation from the sample. Thus, it is expected that in other embodiments the detector 13 could be placed outside of the cavity, or behind an infrared transparent material provided that the photo sensor 13 is in a position to detect the infrared radiation from the sample.

The invention's infrared-photosensor, which determines sample temperature, does not interfere with the measurement of the sample's weight. This is so even though the photosensor measures the actual, average temperature of the sample and not merely the air temperature surrounding the sample. Such infrared analysis leads to a more accurate and precise temperature measurement as compared to a probe or the like, which measures only at a discrete, localized part of the sample. In other words, the infrared- photo sensor provides accurate, non-contact temperature measurements. This facilitates control of the applied microwave energy, resulting in improved drying and moisture analysis.

It will be further understood that although an infrared photosensor is a preferred device for measuring the sample temperature, the invention is not limited to infrared photosensors. The invention can incorporate other sensing devices and techniques provided that they accurately measure the sample temperature (rather than the ambient temperature) and do not interfere with the accurate and precise function of the balance.

The apparatus includes an analytical balance of broadly designated at 14 for measuring the weight of the sample 12 while the sample is in the cavity. As schematically illustrated in FIG. 2, an analytical balance typically includes a pan 15 or equivalent sample holder, with the appropriate mechanical or electrical components 16 and 17 associated therewith. Portions of the balance 14 are typically positioned both inside the cavity as well as outside of the cavity 11. The use of analytical balances within microwave devices is generally well understood in this art and will not be repeated herein in any particular detail other than as necessary to describe the invention. Exemplary descriptions of such analytical balances within microwave devices are given for example in commonly assigned U.S. Pat. Nos. 3,909,568; 4,438,500; and 4,457,632.

A power source introduces microwave energy into the cavity 11. In generally preferred embodiments, the power source comprises a magnetron 21 for generating microwaves and a waveguide 22 in wave communication with the magnetron 21 and the cavity 11 for directing microwaves from the magnetron 21 to the cavity 11 and thus to the sample 12. The generation and propagation of microwaves from magnetrons through waveguides into cavities is generally well understood in this art and will not be described in further detail herein. It will be recognized, however, that there are additional sources other than magnetrons 21 including klystrons, and a continuously variable power supply which is described and set forth in co-pending and commonly assigned application Ser. No. 09/063,545 filed Apr. 21, 1998, the contents of which are incorporated entirely herein by reference. It is likewise expected that solid state microwave devices, which presently have wide application in communications devices, will eventually be suitable as power sources for microwave assisted chemical analysis including the moisture content analysis described herein.

A processing unit illustrated as the controller 23 is in communication with the infrared sensor 13 and the power source 21 for controlling the introduction of microwave energy to the cavity 11 in response to the infrared photosensor 13 to prevent the sample 12 in reaching temperatures at which the sample would burn. Stated somewhat differently, the controller controls or moderates the microwave power or microwave propagation that reaches the sample when the sample temperature begins to approach a temperature at which the sample would burn.

In this regard, it will be understood that much of the testing carried out on samples is done repeatedly on samples of known characteristics; i.e., a given food product such as cheese. Thus, the selection of a predetermined set point is relatively straightforward for those of skill in the art. Indeed, even if the moisture content or burning temperature of a given material is completely unknown, the sample can be tested in the device to identify these parameters relatively quickly and easily and without undue experimentation.

Because the general features and operation of control systems are well known in the art, the selection of the controller and its operation can be carried out by those of ordinary skill in these arts and without undue experimentation. Exemplary control devices and circuits are set forth in a variety of sources including by way of example and not limitation, Dorf, *The Electrical Engineering Handbook*, 2nd Edition (1997) by CRC Press, for example in Chapters 79–85 and 100.

FIG. 2 also schematically illustrates the appropriate circuitry 24 that connects the controller 23 to the source 21 and circuitry 25 that connects the controller 23 to the infrared photosensor 13. In the same manner, and in preferred embodiments, the controller 23 is in communication with the balance 14 through the appropriate circuitry 26 for controlling the introduction of microwave energy to the sample 12 in response to the measured weight of the sample. Stated differently, the controller stops the device from operating further when the sample is dry.

The controlled relationship among the power source, the temperature sensor, and the balance also permits the apparatus of the invention to perform various other tasks, such as thermogravimetric analysis, for which previous microwave devices have been less satisfactory.

There are a number of techniques for determining the endpoint of a drying-type moisture determination, any of which can be suitably incorporated with the apparatus and methods of the present invention. By way of example and not limitation, the endpoint can be defined when the weight of the sample remains constant for a defined period of time, or for a defined number of consecutive measurements. Alternatively, and as described for example in commonly assigned U.S. Pat. Nos. 3,909,568; 4,438,500; and 4,457,632, the mathematical relationship between drying time and moisture content can be used to predict when the endpoint will be reached even if the sample is not dried out completely. These or any other appropriate techniques can be used in conjunction with the apparatus and method of this invention.

FIG. 2 further illustrates preferred embodiments of the invention that include an exhaust fan 27 for removing volatiles from the cavity 11 as the sample 12 is being heated therein. In the most preferred embodiments, the exhaust fan 27 is a variable speed fan and is communication with the processing unit 23 through the appropriate circuitry 30 to control the speed of the fan 27 in response to the infrared photosensor 13 and the analytical balance 14. In this manner, the fan 27 can help prevent the flow of exhausted volatile materials from affecting the measurements of the analytical balance and can likewise provide a moderating effect on the temperature within the cavity 11 as may be desired. Those familiar with the operation and characteristics of such analytical balances, and particularly when they are used with small samples and small weight changes, will understand that air movement within the cavity 11 can aerodynamically affect the balance pan 15 and thus reduce the accuracy and precision of the balance 14.

FIG. 3 illustrates another embodiment of the invention in which the elements are commonly numbered with those of FIG. 2 for the sake of clarity, but which further illustrates a microwave absorbing material shown as the susceptor 31 in the cavity for absorbing microwaves and converting the absorbed microwaves into thermal energy that heat the sample.

The term "susceptor" is used herein in its broadest sense; i.e., an object or material that absorbs microwave radiation and converts the energy to heat. The susceptor can be formed of any material that absorbs microwaves and converts the energy to heat, provided that the susceptor material avoids otherwise interfering with the overall process. Certain ceramic materials such as silicon carbide (SiC) are typically used to form microwave susceptors, but it will be understood that the use of a susceptor is not limited to ceramics or silicon carbide. In common usage in the microwave arts, the term "susceptor" often refers to a thin film material with the desired characteristics, and as used herein, the term "susceptor" includes this meaning as well. As illustrated in FIG. 3, the microwave absorbing material is usually either in close proximity or direct contact with the sample 12 to most efficiently enable the heat transfer desired.

The use of the susceptor, when combined with the temperature measurement and control of the present invention, provides an apparatus and method that takes full advantage of microwave techniques, and extends the use of microwaves to the temperature-controlled treatment of materials that would normally be unresponsive to, or would suffer degradation under, the application of microwave radiation.

FIG. 1 illustrates the appearance of a typical commercial version of the apparatus 10 and illustrates a viewing area 32, normally comprising a combination of a shatter proof glass and a metal screen, a door defined by the dotted line 33 for providing easy access to the cavity 11, a control panel broadly designated at 34 for providing the appropriate starting or operational instructions to the device, and a display 35 that typically incorporates light emitting diodes (LEDs) or liquid crystal displays (LCDs) to provide information to the operator. The apparatus 10 can also provide its output in digital form as may be desired or necessary; e.g., Dorf, supra, Section VIII "Digital Devices."

In another aspect, the invention is a method for measuring moisture content of a sample that is particularly suitable for samples that tend to burn when heated. In this aspect, the invention comprises the steps of applying microwave radiation at a predetermined power level to a moisture containing sample to drive moisture from the sample while continuously weighing the sample. The predetermined power level is low enough to be expected to prevent burning and the continuous weighing of the sample preferably comprising monitoring both the weight and the weight change of the sample. As set forth with respect to the method aspects of the invention, the microwave power is typically (but not exclusively) applied by generating the microwaves in a source, propagating the microwaves from the source through a waveguide, and thereafter launching the microwaves into a cavity in which the sample is located. It will be understood, of course, by those of ordinary skill in this art, that the use of the waveguide and the launcher are typically considerations of space and geometry and are not necessarily required provided that microwaves are otherwise appropriately introduced to the sample.

The method further comprises monitoring the temperature of the continuously weighed sample during the application of microwaves without contacting either the sample or anything in contact with the sample. In the most preferred embodiments, the step of monitoring the sample temperature comprises monitoring the infrared radiation emitted by the heated sample, as this provides a preferred method of obtaining an accurate temperature of the sample without contacting it.

The microwave power applied to the sample is moderated based upon the monitored temperature to maintain the temperature of the sample at or below a predetermined set point temperature below which the sample will not burn. Microwave power can be moderated using several different techniques which generally fall into the categories of moderating the microwave power produced by the source, or moderating the passage of microwaves between the source and the sample. As set forth above, commonly assigned and co-pending application Ser. No. 09/063,545, filed Apr. 21, 1998, discloses a method for moderating the power at the source, while commonly assigned U.S. Pat. No. 5,796,080 discloses an apparatus and technique for moderating the passage of microwaves between a source and sample, and the contents of this are incorporated entirely herein by reference.

In a somewhat different aspect, the method comprises applying microwave radiation at a predetermined power level low enough to be expected to prevent burning to a moisture containing sample to drive moisture from the sample while continuously weighing the sample; monitoring the infrared radiation emitted by the continuously weighed sample and its surroundings during the application of microwave power without contacting either the sample or anything in contact with the sample; converting the value of the emitted infrared radiation into a temperature measurement; moderating the microwave power being applied to the sample based upon the measured temperature to maintain the temperature of the sample at or below a predetermined set point temperature below which the sample will not burn as moisture leaves the continuously weighed sample; and ending the application of microwave power when the weight loss of the sample indicates that the sample is dry. As noted above with respect to the apparatus aspects of the invention, there are a number of suitable techniques for determining the end point of a drying technique that can be suitably used in conjunction with the method of the invention.

In preferred embodiments, the method comprises measuring the temperature of a sample using an infrared photosensor, and measuring both the initial temperature and the continuous temperature of the sample as the drying process proceeds. The method further comprises measuring an initial weight and then continuously measuring the weight and weight change of the sample using an analytical balance while applying microwave energy to the sample at a predetermined power level that heats the sample without burning the sample. The microwave energy is moderated, usually decreased but possibly increased, in response to the temperature measured by the infrared photosensor in a manner that maintains the temperature of the sample below the temperature at which the sample would burn, while continuing to measure the weight and weight change of the sample with the analytical balance as the sample dries. The application of microwave power to the sample is ended when the measured weight or weight change indicates that the sample is dry.

As set forth with respect to the apparatus aspects of the invention, the method can further comprise the step of removing volatiles generated by the drying sample to thereby enhance the drying process or otherwise control the technique.

In the drawings and specification, there have been disclosed typical embodiments of the invention, and, although specific terms have been employed, they have been used in a generic and descriptive sense only and not for purposes of limitation, the scope of the invention being set forth in the following claims.

That which is claimed is:

1. An apparatus for determining the volatile content of a sample while monitoring or controlling the sample temperature, the apparatus comprising:

a cavity in which a sample for which the volatile content is to be determined can be placed;

an infrared temperature sensor capable of measuring and positioned to measure the infrared radiation emitted by the sample placed within said cavity without contacting the sample;

an analytical balance for measuring the weight of the sample while the sample is in said cavity;

a power source for introducing microwaves into said cavity that have frequencies substantially other than the infrared frequencies; and a processing unit in communication with said temperature sensor and said power source for controlling the introduction of said frequencies of microwave energy into said cavity in response to the infrared frequencies measured by said temperature sensor to control the sample temperature until the microwaves from said source dry the sample sufficiently for said processing unit to determine the volatile content of the sample based on the weight change of the sample on said balance.

2. A volatile content apparatus determining according to claim 1 wherein said temperature sensor comprises an infrared photosensor that measures the temperature of the sample rather than the temperature of the cavity or the ambient surroundings.

3. A volatile content determining apparatus according to claim 1 wherein said processing unit is in communication with said analytical balance for controlling the introduction of microwave energy to the sample in response to the measured weight of the sample.

4. A volatile content determining apparatus according to claim 3 and further comprising an exhaust fan for removing volatiles from said cavity as the sample is being heated therein.

5. A volatile content determining apparatus according to claim 4 wherein:

said exhaust fan is a variable-speed exhaust fan; and said processing unit is in communication with said fan for controlling the speed of said fan in response to said temperature sensor and said analytical balance.

6. A volatile content determining apparatus according to claim 1 wherein said power source is selected from the group consisting of magnetrons, klystrons, and solid state devices for generating microwaves.

7. A volatile content determining apparatus according to claim 1 comprising a waveguide for directing microwaves from said source to said cavity.

8. A volatile content determining apparatus according to claim 1 and further comprising a microwave absorbing material in said cavity for absorbing microwaves and converting the absorbed microwaves into thermal energy that heats the sample.

9. A volatile content determining apparatus according to claim 8 wherein said microwave absorbing material is positioned to be in thermally conductive contact with the sample.

10. A volatile content determining apparatus according to claim 6 wherein said microwave absorbing material comprises a susceptor.

11. An apparatus for determining volatile content of a sample while controlling the sample temperature, the apparatus comprising:

a cavity for holding a sample;

a magnetron for generating microwave energy that has a frequency substantially other than the infrared frequencies;

a waveguide for directing microwave energy from said magnetron to said cavity;

an infrared photosensor positioned to measure the infrared radiation emitted by the sample placed within said cavity;

an analytical balance for measuring the weight of the sample placed within said cavity;

a susceptor in said cavity for absorbing microwaves and converting the absorbed microwaves into thermal energy;

a variable-speed exhaust fan for removing volatiles from said cavity; and a processing unit in communication with said magnetron, said infrared photosensor, said analytical balance, and said variable speed exhaust fan for controlling the introduction of said frequencies of microwaves into said cavity in response to the infrared frequencies measured by said infrared photosensor, said analytical balance, and said variable-speed exhaust fan to prevent the sample from reaching temperatures at which the sample would burn, until the microwaves from said source dry the sample sufficiently for said processing unit to determine the volatile content of the sample based on the weight change of the sample on said balance.

12. A method for determining volatile content of a sample while controlling the sample temperature, the method comprising:

measuring the infrared radiation emitted by a sample using an infrared photosensor;

measuring the weight of the sample using an analytical balance;

applying microwave energy that has a frequency substantially other than the infrared frequencies to the sample at a predetermined power level that heats the sample without burning the sample; and moderating the microwave energy applied to the sample in response to the infrared radiation measured by the infrared photosensor in a manner that maintains the temperature of the sample below the temperature at which the sample would burn while continuing to measure the weight of the sample with the analytical balance as the sample dries; and ending the application of microwave power to the sample when sufficient volatiles have been driven from the sample to calculate the volatile content of the sample.

13. A method of determining volatile content according to claim 12 further comprising measuring an initial weight of the sample prior to applying the microwave energy to the sample.

14. A method of determining volatile content according to claim 12 further comprising measuring an initial temperature of the sample prior to applying the microwave energy to the sample.

15. A method of determining volatile content according to claim 12 wherein the step of measuring the weight of the sample comprises continuously measuring the weight of the sample as the microwave power is being applied.

16. A method of determining volatile content according to claim 12 wherein the step of measuring the temperature of the sample comprises continuously measuring the temperature of the sample as the microwave power is being applied.

17. A method of determining volatile content according to claim 12 and further comprising removing the volatiles generated by the drying sample.

18. A method of determining volatile content according to claim 12 wherein the step of applying microwave energy to the sample comprises:

generating the microwave s in a source;

propagating the microwaves from the source through a waveguide; and launching the microwaves into a cavity in which the sample is located.

19. A method of determining volatile content according to claim 18 wherein the step of moderating the microwave energy comprises moderating the microwave power produced by the source.

20. A method of determining volatile content according to claim 18 wherein the step of moderating the microwave energy comprises moderating the passage of microwaves between the source and the cavity in which the sample is located.

21. A method of determining volatile content according to claim 12 wherein the step of ending the application of microwave power comprises ending the application of microwave power to the sample when the measured weight indicates that the sample is dry.

22. A method for determining moisture content of a sample that is particularly suitable for samples that tend to burn when heated, the method comprising:

applying microwave radiation that has a frequency other than the infrared frequencies at a predetermined power level to a moisture-containing sample to drive moisture from the sample;

monitoring the weight of the sample during the application of microwave power;

monitoring the infrared radiation emitted by the sample during the application of microwave power without contacting either the sample or anything in contact with the sample; and moderating the microwave power being applied to the sample based upon the monitored infrared radiation to maintain the temperature of the sample at or below a pre-determined set point temperature below which the sample will not burn, until the weight change in the sample is sufficient to calculate the moisture content of the sample.

23. A method of determining moisture content according to claim 22 wherein the step of monitoring the weight of the sample during the application of microwave power comprises continuously monitoring the weight of the sample during the application of microwave power.

24. A method of determining moisture content according to claim 22 wherein the step of monitoring the temperature of the sample during the application of microwave power comprises continuously monitoring the temperature of the sample during the application of microwave power.

25. A method of determining moisture content according to claim 22 comprising ending the application of microwave power to the sample when the sample reaches a predetermined temperature.

26. A method of determining moisture content according to claim 22 wherein the step of monitoring the temperature of the sample comprises monitoring the infrared radiation emitted by the heated sample.

27. A method of determining moisture content according to claim 22 and further comprising removing the volatiles generated by the drying sample.

28. A method of determining moisture content according to claim 22 wherein the step of applying microwave radiation to the sample comprises:

generating the microwaves in a source;

propagating the microwaves from the source through a waveguide; and launching the microwaves into a cavity in which the sample is located.

29. A method of determining moisture content according to claim 28 wherein the step of moderating the microwave energy comprises moderating the microwave power produced by the source.

30. A method of determining moisture content according to claim 28 wherein the step of moderating the microwave energy comprises moderating the passage of microwaves between the source and the cavity in which the sample is located.

31. A method for determining moisture content of a sample that is particularly suitable for samples that tend to burn when heated, the method comprising:

applying microwave radiation that has a frequency other than the infrared frequencies at a predetermined power level to a moisture-containing sample to drive moisture from the sample while continuously weighing the sample;

monitoring the infrared radiation emitted by the continuously-weighed sample and its surroundings during the application of microwave power without contacting either the sample or anything in contact with the sample;

converting the value of the emitted infrared radiation into a temperature measurement;

moderating the microwave power being applied to the sample based upon the monitored infrared radiation and the converted temperature to maintain the temperature of the sample at or below a pre-determined set point temperature below which the sample will not burn as moisture leaves the continuously-weighed sample; and ending the application of microwave energy when the weight loss of the sample is sufficient to calculate the moisture content of the sample.

32. A method of determining moisture content according to claim 31 wherein the step of monitoring the infrared radiation emitted by the continuously-weighed sample and its surroundings comprises continuously monitoring the infrared radiation emitted by the continously-weighed sample and its surroundings.

33. A method of determining moisture content according to claim 31 and further comprising removing the volatiles generated by the drying sample.

34. A method of determining moisture content according to claim 31 wherein the step of applying microwave radiation to the sample comprises:

generating the microwaves in a source;

propagating the microwaves from the source through a waveguide; and launching the microwaves into a cavity in which the sample is located.

35. A method of determining moisture content according to claim 34 wherein the step of moderating the microwave energy comprises moderating the microwave power produced by the source.

36. A method of determining moisture content according to claim 34 wherein the step of moderating the microwave energy comprises moderating the passage of microwaves between the source and the cavity in which the sample is located.

37. A method of determining moisture content according to claim 31 wherein the step of applying microwave radiation at a predetermined power level comprises applying microwave radiation at a predetermined power level to the sample and a susceptor.

38. A method of determining moisture content according to claim 37 wherein the step of monitoring the infrared radiation comprises monitoring the infrared radiation emitted by the sample and the susceptor during the application of microwave power without contacting the sample or susceptor.

* * * * *

UNITED STATES PATENT AND TRADEMARK OFFICE
CERTIFICATE OF CORRECTION

PATENT NO. : 6,227,041 B1　　　　　　　　　　　　　　　　　　　　　　Page 1 of 1
DATED : May 8, 2001
INVENTOR(S) : Collins et al.

It is certified that error appears in the above-identified patent and that said Letters Patent is hereby corrected as shown below:

Title page,
ABSTRACT, lines 3 and 14, "bum" should be -- burn --

Signed and Sealed this

Twelfth Day of March, 2002

Attest:

JAMES E. ROGAN
*Attesting Officer*　　　　*Director of the United States Patent and Trademark Office*